United States Patent
Molino et al.

(10) Patent No.: US 10,835,409 B1
(45) Date of Patent: Nov. 17, 2020

(54) APPARATUS FOR CORRECTION OF LEG DEFORMITIES

(71) Applicants: Joseph L. Molino, Valley Cottage, NY (US); Michael Rebarber, Glen Rock, NJ (US)

(72) Inventors: Joseph L. Molino, Valley Cottage, NY (US); Michael Rebarber, Glen Rock, NJ (US)

( * ) Notice: Subject to any disclaimer, the term of this patent is extended or adjusted under 35 U.S.C. 154(b) by 0 days.

(21) Appl. No.: 16/694,759

(22) Filed: Nov. 25, 2019

(51) Int. Cl.
*A61F 5/00* (2006.01)
*A61F 5/01* (2006.01)

(52) U.S. Cl.
CPC .......... *A61F 5/0127* (2013.01); *A61F 5/0125* (2013.01); *A61F 2005/0146* (2013.01)

(58) Field of Classification Search
CPC .... A61F 5/0123; A61F 5/0111; A61F 5/0127; A61F 5/0585; A61F 5/14
USPC ...................................... 602/26, 25
See application file for complete search history.

(56) References Cited

U.S. PATENT DOCUMENTS

| | | | | |
|---|---|---|---|---|
| 2,516,872 A | * | 8/1950 | Hauser | A61F 5/0127 602/27 |
| 5,242,378 A | * | 9/1993 | Baker | A61F 5/0102 602/23 |
| 7,147,612 B2 | | 12/2006 | Molino et al. | |
| 7,462,159 B1 | * | 12/2008 | Shlomovitz | A61F 5/0102 602/16 |
| 2016/0058595 A1 | * | 3/2016 | Tsitouras | A61F 5/0113 602/28 |
| 2016/0175134 A1 | * | 6/2016 | Ghahfarokhi | A61F 5/0127 602/16 |
| 2016/0287423 A1 | * | 10/2016 | Ramirez | A61F 2/68 |

* cited by examiner

*Primary Examiner* — Kim M Lewis
(74) *Attorney, Agent, or Firm* — Lawrence G. Fridman, ESQ; Feigin & Fridman, LLC

(57) ABSTRACT

An orthotic medical device, including a proximal receiving element receiving part of an upper area of a human limb and a distal receiving element receiving part of a lower area of the human limb. The distal receiving element, with part of the lower limb area are pivotally movable with respect to the proximal receiving element. A foot supporting arrangement is adapted to receive at least a portion of a foot of the human limb, A first ankle joint, is fixedly attached to the foot supporting arrangement and to the distal receiving element on a first, and a second ankle joint arrangement is disposed on a second side and includes a rigid elongated element slidably disposed within a channel in the distal region of the distal receiving element, and an ankle joint fixedly attached to the foot supporting arrangement and to a distal end of the rigid elongated element.

12 Claims, 6 Drawing Sheets

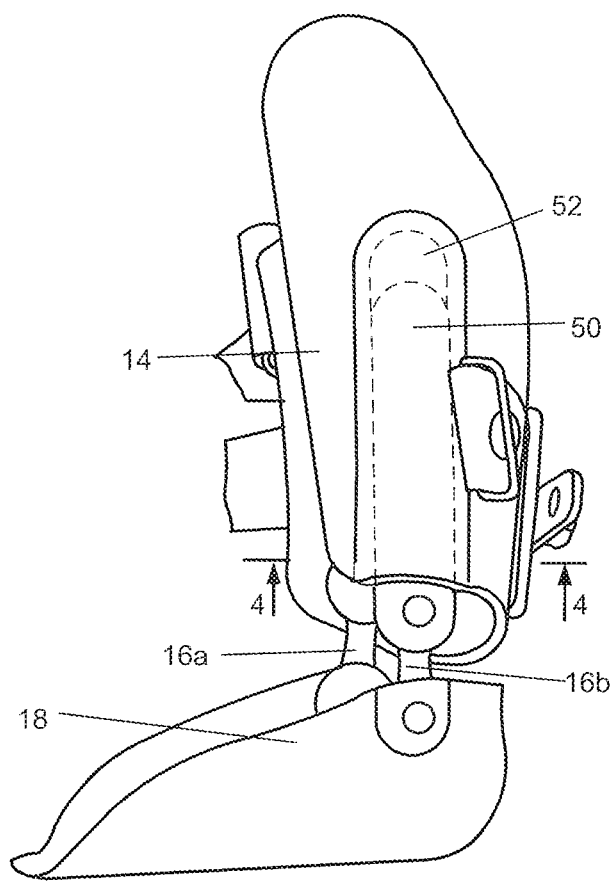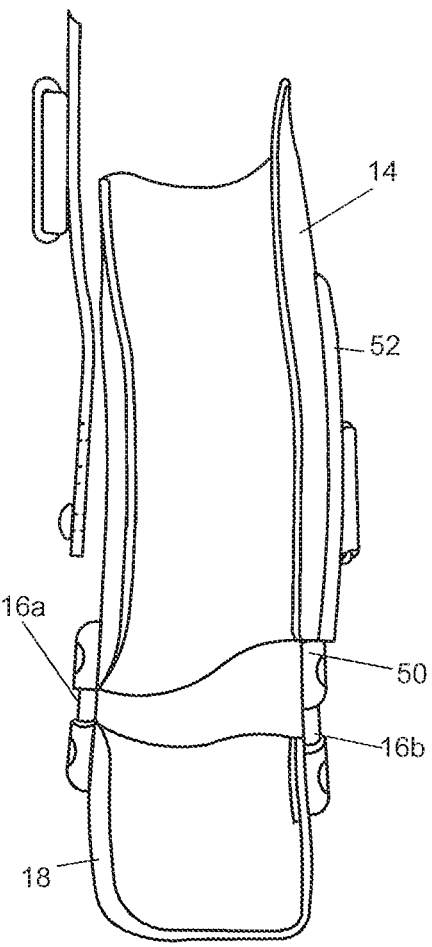
FIG. 3  FIG. 5
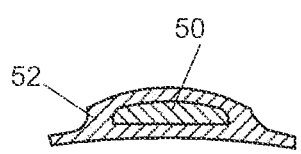
FIG. 4

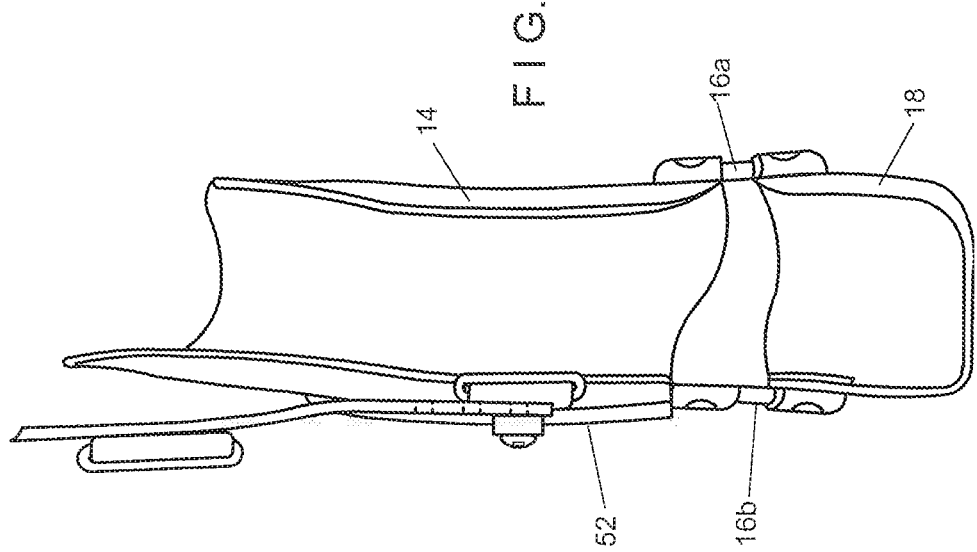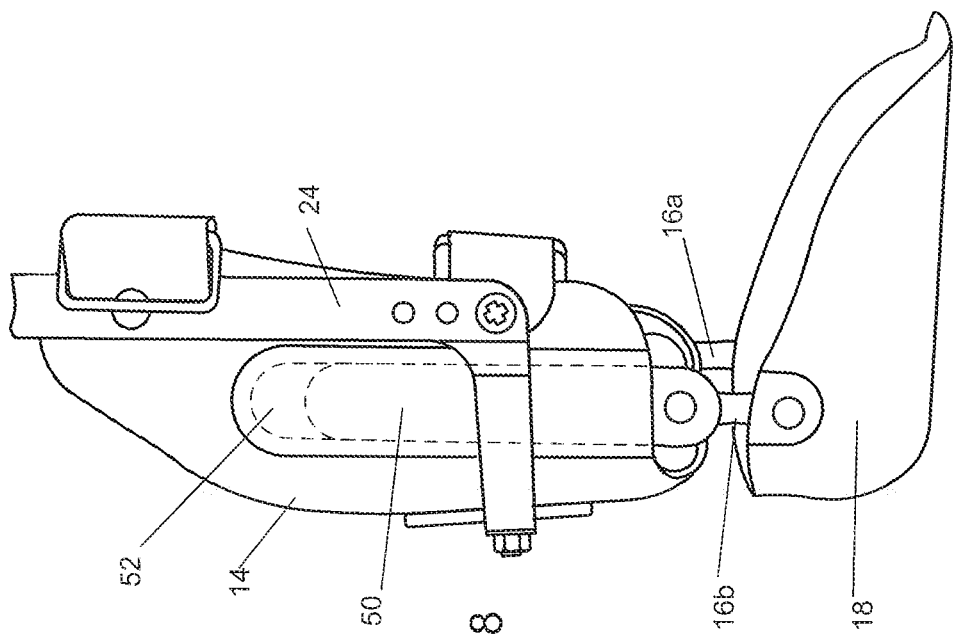

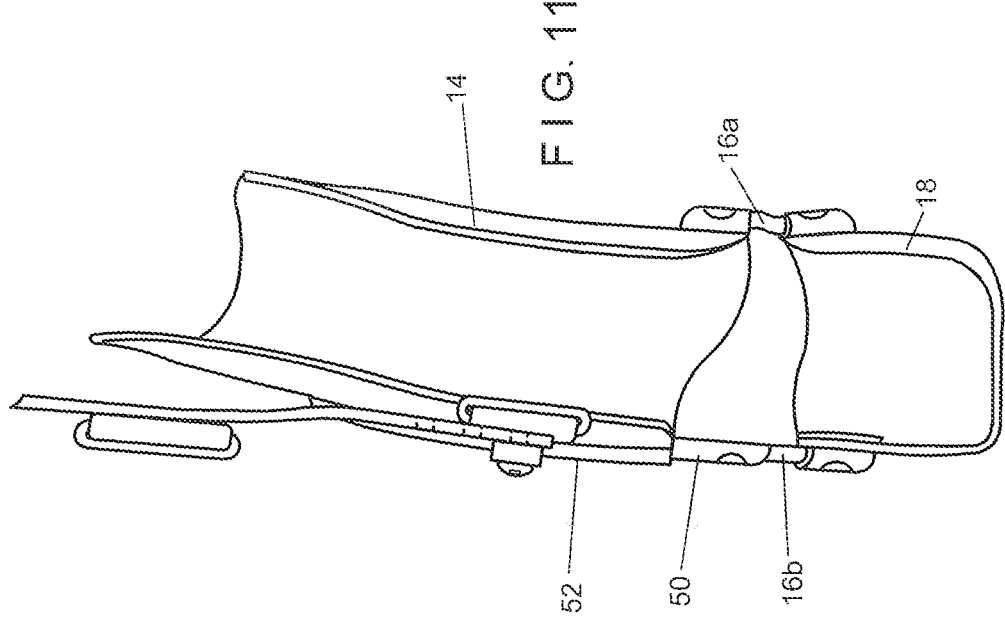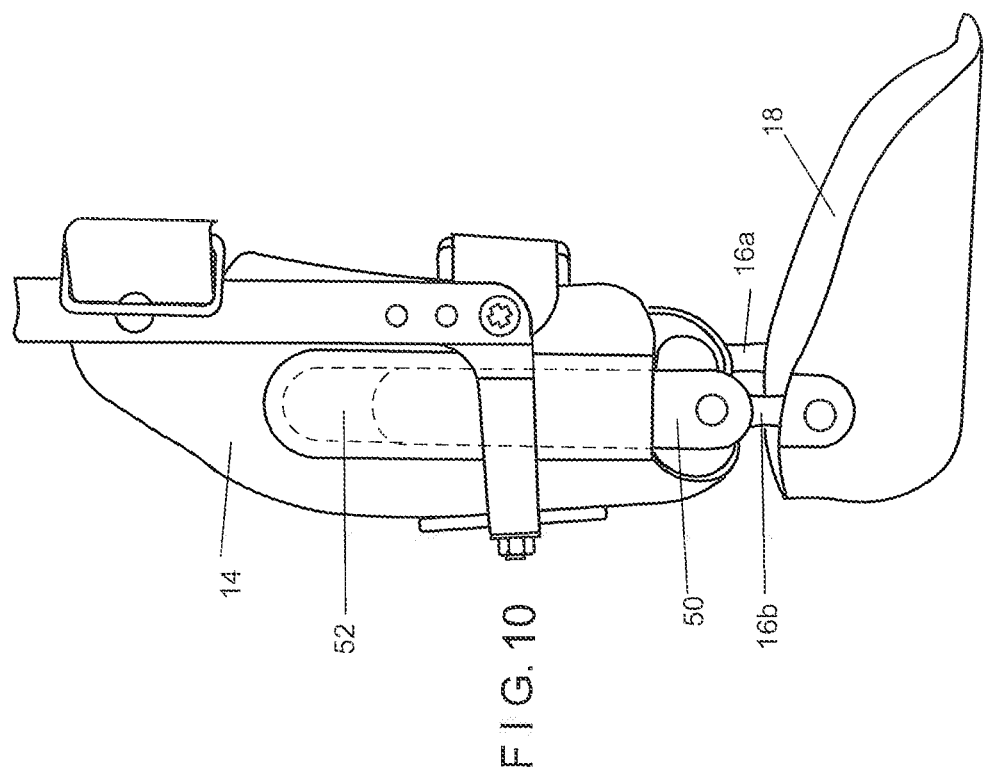

APPARATUS FOR CORRECTION OF LEG DEFORMITIES

FIELD OF THE INVENTION

The present invention relates generally to medical devices, and more specifically, it relates to an orthotic device for correction of leg deformities.

BACKGROUND OF THE INVENTION

Blount's disease is a progressive disease that affects the varus angle of the tibia in children that is correctable with proper treatment. This disease is a progressive developmental condition that is characterized by disordered endochondral ossification of the medial tibial physis. This results in an abrupt varus deformity in the proximal tibia and is also associated with an internal torsion of the tibia. Current treatment of Blount's disease includes use of static orthotic devices or surgical procedure also known as tibial osteotomy. These procedures can create other misalignments, are incremental, and unnecessarily slow.

There are two forms of Blount's disease recognized. First is an infantile form of the disease which occurs prior to three years of age, Second is an adolescent form which occurs after age eight. Diagnostic characteristics of Blount's disease consist of sharp Varus angulations in the metaphysis, a widened and irregular physeal line medially, a medially sloped and irregularly ossified epiphysis, and a prominent breaking of the medial metaphysis, with lucent cartilage islands in the beak. Additional symptoms include pain, progressive bowing, an abnormal gait, and leg length discrepancies. The cause of Blount's disease is currently unknown.

The nature of Blount's Disease is in the bowing of the tibial portion of the leg and is based on the diminished growth capacity of the medial area of the tibia and a continued normal growth emanating from the lateral area of the tibia. This condition results in the normal growth of the lateral portion of the tibia, while growth of the medial portion of the tibial shaft is suppressed. The abnormality exists due to the continued growth of the lateral epiphysis and the stunted growth of the medial epiphysis causing a curving of the leg. This causes the outward bowing of the tibia which usually occurs in infants and is most prominent just after they start walking.

Currently, the disease is treatable by application of conventional braces with limited success and an unnecessarily long treatment period. The known prior art devices utilized for the correction of the tibia are very restrictive in nature and are typically utilized when the leg of a patient is in a straight position. The conventional medical devices utilized for treatment of Blount's disease are based on the application of a three-point pressure system. The typical application of the three point pressure system is as follows: (1) the proximal most portion of the brace is adapted to produce a counter force at the upper portion of the inner femur; (2) the most distal portion of the brace generates a counter force at the ankle; and (3) the corrective pressure is exerted by pressure from the lateral side towards the medial counter forces. Unfortunately, during application of the three-point pressure system, deformation and correction occurs not only at the tibia, which needs to be corrected, but the compensatory deformation and correction of the bone structure also occurs at the femur, which does not need to be corrected. During this prior art procedure often a perfectly normal and healthy bone is involved in the corrective process by introducing forces that are typically unnecessarily adapted to bend and deform the femur. Review of the mechanics of Blount's disease conducted by the prior art devices leads to the conclusion that correction of the affected part, namely the tibia, is the primary concern in the treatment of patients and not the treatment of the femur. This is because the treatment of the femur introduces additional and undesired deformity to the child's limb.

Since it is known that Blount's disease occurs typically with weight-bearing, bracing devices and methods adapted for treatment of this disease should be effective throughout all phases of the patient's activity. To minimize the progression of Blount's disease, the epiphyseal plate of the tibia needs to be aligned correctly while ambulating. Then the tibia will correct itself, as shown in the prior art study.

The orthotic device disclosed by U.S. Pat. No. 7,147,612 includes a single ankle joint on one side of the user's leg and is completely free on the opposing side. As such, there is a chance that the foot receiving element thereof would swing away from the distal receiving element on the side that does not include an ankle joint. In some situations, this may expose the user's foot and might cause for the user to trip on and fall.

Thus, there has been a long felt and unsolved need for a medical device and procedure adapted for treatment of Blount's disease and capable of overcoming the shortcomings of the prior art. Specifically, there has been a need for a medical device which is capable of isolating the corrective forces and directing them for treatment of the distal portion of the leg or treating the tibial bone without affecting the Femur bone or etching the medial collateral ligament (which is attached to the femur and to the tibia and is responsible for holding the knee joint together in the Coronal plane on the medial side of the leg).

It has been also a need for an orthotic device ensuring that the foot receiving element is connected to the distal receiving element on both sides, wherein one of the connections is dynamic to facilitate engagement of the users foot with the floor at all times.

SUMMARY OF THE INVENTION

In the device of the invention, a focused, dynamic force is applied to the tibia so as to generate a required correction, for example for Varus or Valgus conditions, Such focused application of the corrective forces does not introduce deforming forces to the unaffected portions of the limb. The corrective forces are specifically directed at the area of the varusor Valgus malformation, while not affecting the femur, the medial collateral ligament, the distal tibia or ankle complex.

In accordance with an aspect of an embodiments of the present invention, there is provided an orthotic medical device, including a proximal receiving element adapted to receive at least a portion of an upper area of a human limb, the proximal receiving element being substantially stationary with respect to the upper limb area. The orthotic device further includes a distal receiving element adapted to receive at least a portion of a lower area of the human limb, the distal receiving element having at least proximal and distal regions spaced from each other, the distal receiving element with the at least a portion of the lower limb area being pivotally movable with respect to the proximal receiving element by forces applied at the proximal region of the distal receiving element. A foot supporting arrangement is adapted to receive at least a portion of a foot of the human limb.

A first ankle joint, is fixedly attached to the foot supporting arrangement and to the distal region of the distal receiving element on a first side of the distal receiving element, and a second ankle joint arrangement is disposed on a second, opposing side, of the distal receiving element, and includes a rigid elongated element slidably disposed within a channel formed in the distal region of the distal receiving element, and an ankle joint fixedly attached to the foot supporting arrangement and to a distal end of the rigid elongated element. As such, on the second side, the distance of the foot supporting arrangement from the distal receiving element is dynamic and adjustable by sliding motion of the rigid elongate element within the channel in a distal/proximal direction.

In some embodiments, the first side is the lateral side of the distal receiving element, and the second side is the medial side of the distal receiving element. In other embodiments, the first side is the medial side of the distal receiving element, and the second side is the lateral side of the distal receiving element.

In some embodiments, the first ankle joint is substantially rigid in the proximal to distal direction and is substantially flexible in the Coronal and Sagittal planes. In some such embodiments, the pivotal motion of the distal receiving element and the portion of the lower limb area received thereinside does not affect orientation of the bottom of the foot situated within the foot supporting arrangement with respect to the ground.

In some embodiments, the orthotic medical device further includes a proximal connecting element associated with the proximal receiving element, a distal connecting element associated with the distal receiving element, and a knee joint pivotally connecting the proximal and distal connecting elements.

In some such embodiments, the orthotic medical device further includes a resilient corrective element extending between the distal connecting element and the proximal region of the distal receiving element, and adapted to apply pivotal forces to the proximal region of the distal receiving element.

In some further embodiments, the orthotic medical device further includes an adjustable member movable along the distal connecting element, and a medial connector extending outwardly from the adjustable member, so as to be associated with the distal receiving element and facilitate movement of the distal receiving element along the distal connecting element.

In some embodiments, the adjustable member can be fixedly attached at a predetermined location on the distal connecting element and a pivotal connection is provided between the medial connector and the distal receiving element.

In some embodiments, the proximal receiving element and the medial connector are fixedly positioned with respect to the knee joint.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 3 is a lateral side elevational view of a distal portion of the orthotic device of FIG. 1, in accordance with some embodiments of the invention, in a first, retracted operative orientation;

FIG. 4 is a sectional illustration taken along section lines 4-4 in FIG. 3;

FIG. 5 is an anterior elevational view of the distal portion of the orthotic device of FIG. 3;

FIG. 8 is a medial side elevational view of a distal portion of the orthotic device of FIG. 1, in accordance with another embodiments of the invention, in a first, retracted operative orientation;

FIG. 9 is an anterior elevational view of the distal portion of the orthotic device of FIG. 8;

FIG. 10 is a medial side elevational view of the distal portion of the orthotic device of FIG. 8, in a second, extended operative orientation; and FIG. 11 is an anterior elevational view of the distal portion of the orthotic device of FIG. 10.

DETAIL DESCRIPTION OF THE INVENTION

When using the device of the present invention, a focused, dynamic force is applied to the tibia so as to generate required correction. Such focused application of the corrective forces does not introduce deforming forces to the unaffected portions of the limb. The corrective forces are specifically directed at the area of a varus malformation, while not affecting the femur, the medial collateral ligament, the distal tibia or the ankle complex.

Figure 1:
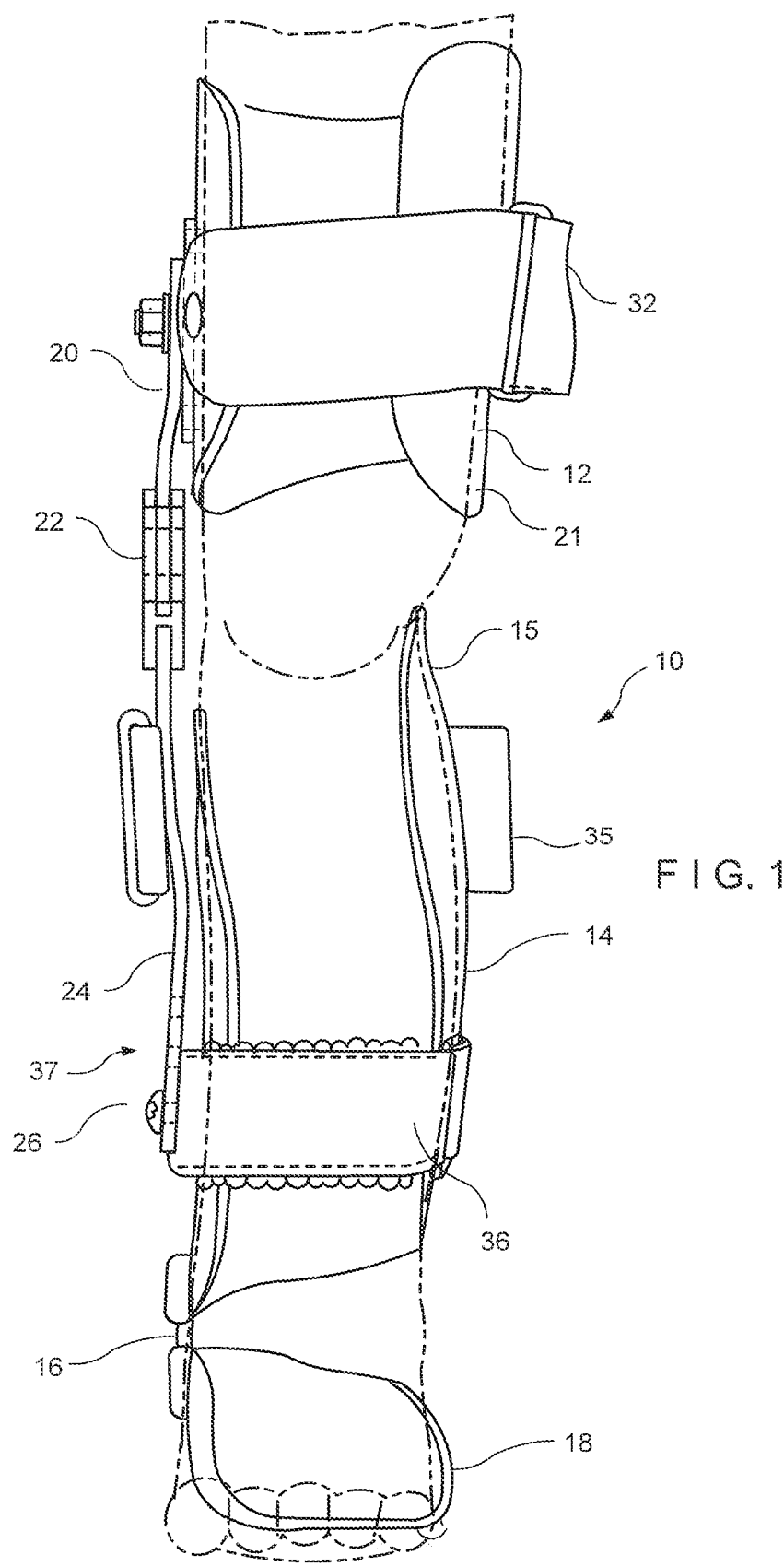
FIG. 1 is a front or anterior elevational view of an orthotic device in accordance with one embodiment of the present invention.
Figure 2:
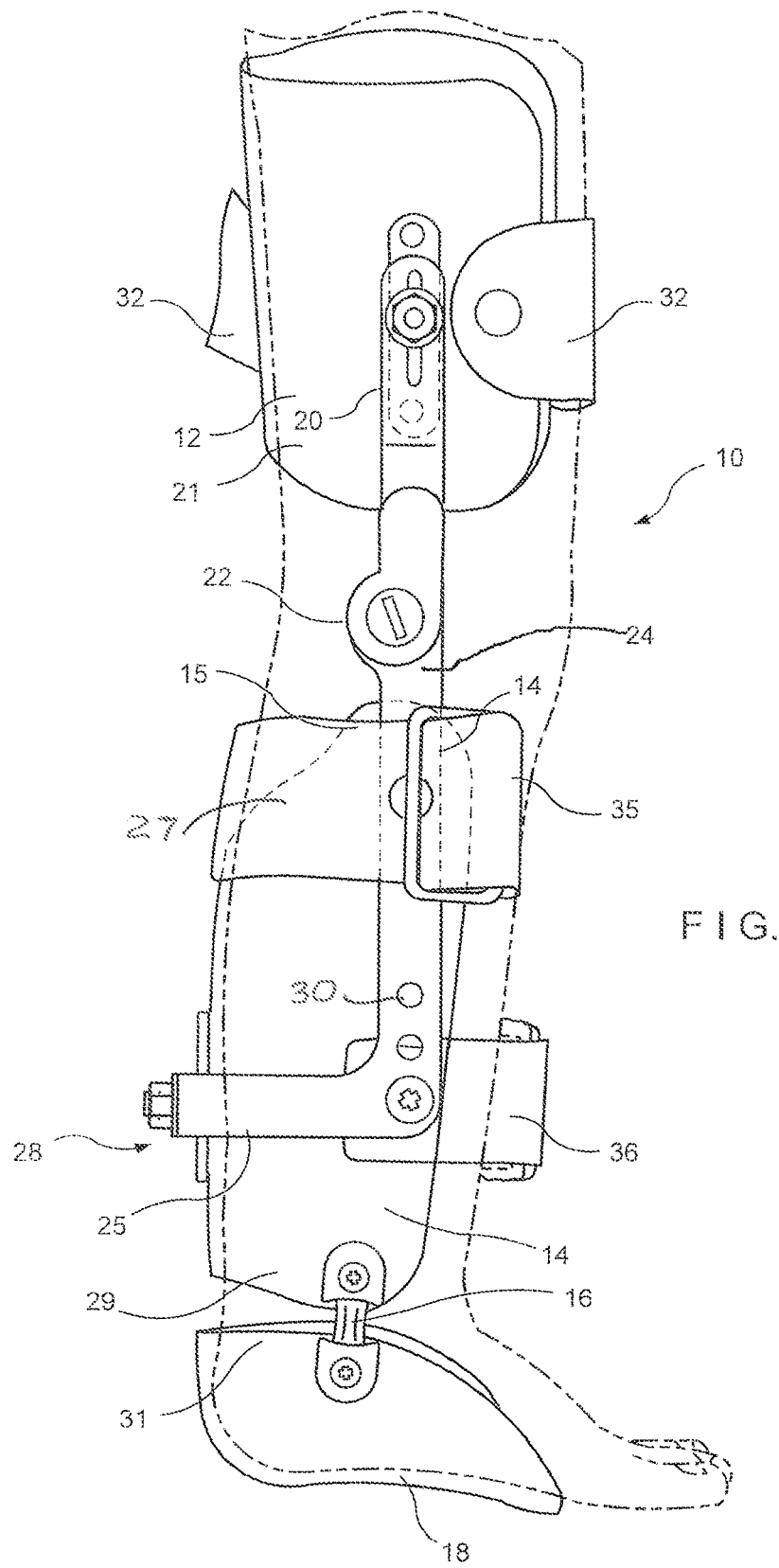
FIG. 2 is a medial side elevational view of the orthotic device of FIG. 1.

Reference is now made to FIG. 1, which is a front or anterior elevational view of an orthotic device 10 in accordance with one embodiment of the present invention, and to FIG. 2, which is a medial side elevational view of the orthotic device 10.

As seen in FIG. 1, orthotic device 10 includes a proximal cuff or proximal receiving element 12 adapted to receive an upper thigh area of the leg of a user, and a distal tibial cuff or distal receiving element 14 adapted to receive a lower leg area or a calf of the leg of the user. A foot supporting arrangement 18, adapted to receive a foot of the user, is connected to distal receiving element 14 by ankle joints 16 on the medial and lateral sides thereof, as explained in further detail hereinbelow.

A proximal strut or proximal connecting element 20 is attached to proximal receiving element 12, and a distal strut or distal connecting element 24 is connected to distal receiving element 14. Proximal connecting element 20 and distal connecting element 24 are pivotally connected to each other at a knee joint 22. It is a particular feature of the present invention that the proximal receiving element 12 and distal receiving element 14 are pivotally connected to each other by a single pair of proximal and distal connecting elements forming a single knee joint, located on the medial side of device 10.

The cuff of proximal receiving element 12 and the cuff of distal receiving element 14 may each be formed of a semi-resilient material.

In some embodiments, the proximal and distal receiving elements may have a front longitudinal opening adapted to facilitate insertion of the respective leg portion into the interior area thereof. In other embodiments, the proximal and distal receiving elements may have a rear opening adapted to facilitate insertion of the respective leg portion into device 10.

In some embodiments of the invention, the proximal receiving element 12 is adapted to receive the thigh region of the leg from an area just below the greater trochanter on the lateral side, to approximately one inch distal to the perineum on the medial side, A distal region 21 of the proximal receiving element 12 extends to an area just above the medial and lateral femoral chondyles of the femur.

Distal receiving element 14 includes a proximal region 27, which is adapted to terminate well above the fibula neck. In some embodiments, reliefs are provided within the inner area of the element 14 to avoid or minimize contact with the fibula neck and fibula head, in order to avoid impingement of the device on the sensitive areas of the peroneal nerve and fibula head. An extension 15 may extend outwardly from proximal region 27 of distal receiving element 14, Extension 15 is adapted for better engagement with au adjustable elastic corrective element 35. Distal receiving element 14 further includes a distal region 29, which is adapted to terminate just below the midpoint of the gastroc-solieus complex. As explained in further detail hereinbelow, ankle joints 16 connect a proximal region 31 of foot supporting element 18 to distal region 29 of distal receiving element 14. Distal receiving element 14 further includes hook and loop straps and chafes for closure.

An adjustment sub-assembly 37 includes an adjustment member 26 connectable to any one of a plurality of apertures 30 formed in a medial connector 25, which in turn forms part of distal connector 24. Adjustment sub-assembly 37 further includes a pivotal arrangement 28 for adjustment of positioning f the distal receiving element 14 and foot supporting element 18 connected thereto with respect to at least the distal connecting element 24, substantially as described in U.S. Pat. No. 7,147,612, which is incorporated by reference in its entirety as if fully set forth herein.

In some embodiments, the apertures 30 may be disposed at ¼ inch, ½ inch, or ¾ inch increments. The adjustment member 26 then fixes the pivotal arrangement to one of apertures 30.

Adjustment member 26 is adapted for a longitudinal movement along distal connecting element 24, by changing the aperture 30 to which it is connected. In this manner, the position of adjustment member 26 can be adjusted and fixed by any conventional means, at any desirable location below the knee joint 22 on the distal connecting element 24. As such, when the user is a child, the length and arrangement of orthotic device 10 may be adapted to the child's height, as the child grows.

The pivotal arrangement 28 typically includes a pivotal member provided at an area of attachment of the medial connector 25 to the distal receiving element 14. The pivotal arrangement 28, in general, and the pivotal member specifically, have a subjective location depending upon user's physiology. In the preferred embodiment, the pivotal member is positioned on a posterior or rear surface of the distal receiving element 14 in the area corresponding to the location of the apex of the Gastroc Soleus Complex of the leg of the user. In other words, the location of the pivotal member of the distal receiving element 14 may vary from user to user and is typically positioned at the location corresponding to the summit of the belly of the muscle on the back of the user's leg.

In some embodiments, the pivotal member is attached to the posterior region of distal receiving element 14 in the Coronal plane, such that the distal receiving element 14 is capable of moving or pivoting substantially in the same Coronal plane. This means that the element 14 can pivot from the lateral to medial direction and vice versa relative to the distal connecting element 24, while proximal receiving element 12 remains stationary. In some embodiments, the position of medial connector 25 and the connecting elements 20 and 24, relative to the pivotal member, can also be adjusted. In the present invention, knee joint 22 is isolated from and operates independently of the pivotal arrangement 28, so that the knee can flex and move throughout a substantial range of motion independently of the pivoting mechanism, allowing the user to ambulate normally.

When the distal receiving element 14 is allowed to move in the pivotal fashion at the pivotal arrangement 28, such movement does not affect orientation of the bottom of the foot situated in the foot supporting element 18 with respect to the ground surface. One of the main functions of the foot supporting element 18 and the ankle joint 16 is to keep all major elements of the orthotic device 10 at a predetermined elevation or height with respect to the ground. This prevents undesirable distal migration of the elements of the device. In this manner, the knee hinge 22 and the knee center are constantly positioned within the same plane of flexion and proper height to insure a proper location of the center of rotation.

In some embodiments, the device 10 includes at least one proximal holding non-elastic element or a strap 32 associated with the proximal receiving element 12, and at least one distal holding non-elastic element or a strap 36 associated with the distal receiving element 14. The proximal holding element 32 is adapted to hold the thigh portion of the leg confined within an interior area of the proximal receiving element 12. Similarly, the distal holding element or strap 36 is provided for holding the calf area of the same leg confined within the interior area of the distal receiving element 14. Orthotic device 10 may include additional straps similar to straps 32 and 36, associated with either of receiving elements 12 and 14, to hold the respective portion of the human limb within the corresponding receiving element.

As illustrated in FIG. 1, the straps 32, 36 are connected to the respective receiving elements by means of chafes and are formed with tightening/fixing elements in the form of hook and loop connectors also known as Velcro® fasteners, although any other suitable mechanism for tightening or g is considered within the scope of the invention.

A corrective or torsional elastic element 35 is associated with the proximal region 27 of the distal receiving element 14 and is adapted to surround the distal connecting element 24 in the area between the knee joint 22 and the adjustment member 26. By tightening of the elastic or torsional element 35, varying pressure may be applied on the distal receiving element 14 as needed to facilitate application of the medially directed corrective threes to the deformed limb of the user.

Upon tightening, the corrective elastic strap 35 is capable of exerting medially or inwardly directed pressure which causes the proximal region 27 of the distal receiving element 14 and the lower portion of the limb situated thereinside to move or tilt inwardly and the distal region thereof to move or tilt outwardly. More specifically, the action of the elastic corrective element 35 causes an inwardly directed force that pulls the distal receiving element 14 and the lower portion of the limb situated thereinside in the medial direction. As the distal receiving element 14 is tilted, the foot supporting element 18 retains its engagement with the floor. The pressure exerted by corrective element 35 can be adjusted by any conventional means, such as a friction buckle, etc.

The combination of the pivotal arrangement 28 and the corrective resilient element 35 negates the necessity of using a three point pressure system of the prior art, which, as discussed hereinabove, adversely affects the femur and places undue stresses on the bone which does not need to be corrected. The orthotic device 10 specifically directs the majority of the corrective forces only to the tibia, and more specifically directs the dynamic force at the level of the varus deformity. This causes pivotal motion of the distal receiving element 14 in the Coronal plane and generates the corrective force directed at the precise area of deformity without exerting unnecessary forces that are capable of causing ancillary damage to the femur or distal tibia and/or medial collateral ligament.

Most prior art medical devices must be worn when the leg is straight, causing an ambulatory user to walk with a locked knee and with a stiff leg. Therefore, the prior art braces are typically worn while users are sleeping or cause the users to ambulate unnaturally with great difficulty. The dynamic nature of the present invention allows the patient to be normally active. This is because flexion of the knee, facilitated by the knee joint 22, does not affect the corrective forces that are placed on the affected area or the tibia.

Reference is now additionally made to FIGS. 3 to 11. To enhance flexibility of the orthotic device 10, the pair of ankle joints 16 extends between the distal region 29 of the distal receiving element 14 and the proximal region 31 of the foot supporting element 18. As seen in FIGS. 3 and 5-11, a first ankle joint 16a disposed on a first side of the orthotic device 10 is fixedly attached to distal receiving element 14 and to foot supporting element 18, such that it is substantially rigid in the proximal to distal direction, hut is sufficiently flexible in the Coronal and Sagital planes. The second ankle joint 16b, disposed on the second, opposing side of the orthotic device 10, is fixedly connected to foot supporting element 18 and to an elongated surface element 50 which is slidably disposed within a channel 52 formed in the distal receiving element 14. As seen in FIG. 4, elongated surface element 50 substantially fills channel 52, such that it is slidable in the proximal/distal direction, without having the freedom to tilt or twist within the channel.

On the second side, the foot supporting element 18 is allowed to move with respect to the distal receiving element 14 by sliding of surface element 50 within channel 52 in the proximal/distal direction. The interface between receiving element 14, ankle joint 16a, and foot supporting element 18 is necessary to ensure that the orthotic device 10 does not migrate distally. In this manner all hinge surfaces are kept congruent to the actual knee axis and ankle axis. Therefore, V a predetermined position of the adjustment member 26 is reached and it is fixedly attached to the distal connecting element 24, the distances between the axis of the knee joint 22, the longitudinal axis of the medial connector 25, and the axis of the foot supporting element 18 (including the axes of the ankle joints 16a and 16b) remain virtually unchanged during the treatment.

In view of the resiliency of the ankle joint 16 in the Coronal and Sagital planes, as the distal receiving element 14 pivots inward and outward about an axis of ankle joint 16a, and the foot of a patient situated in the foot supporting element 18 is allowed to substantially engage or contact the ground. This occurs throughout the pivotal motion of the distal receiving element 14 and throughout the entire dynamics of the gait pattern. Thus, as dynamic correction is exerted on the proximal portion of the tibia, the foot is allowed to flatly engage the floor.

When there is a correction of the coronally placed hinge causing the foot supporting element 18 to be raised from the surface on medial or lateral side, sliding motion of the elongated surface element 50 within the channel 52 adjusts the arrangement of the foot supporting element 18 to ensure that the foot plate makes total contact with the floor area. In this manner, the corrective forces offered by the force strap 35 pivoting the orthotic device 10 inward or outward are not disrupted. More specifically, as the user walks, the force strap 35 corrects an improper angle shaft cause by the deformity of the leg. While the improper angle is being corrected, elongated surface element 50 slides inward or outward within the channel 52, to ensure total contact of the base of foot supporting element 18 with the walking surface. The sliding of element 50 is typically proportional to the amount of correction achieved by pivoting of pivotal arrangement 28 and by strap 35.

The channel 52 extends substantially vertically within the body of the receiving element 14 between an open end at the distal region and a closed end at the proximal region and is spaced from its front longitudinal opening. In some embodiments, elongated surface element 50 is placed on the plastic cast used for forming the distal receiving element prior to vacuum forming the plastic of the distal receiving element 14 around the cast, so as to form channel 52. A jig vacuum embosses the shape of the elongated surface element 50 onto the vacuum formed plastic to create channel 52. In one embodiment the channel 52 may be formed within the body of distal receiving element 14, In another embodiment the channel 52 may be formed in a space between the body of distal receiving element 14 and an additional piece of plastic covering the body to ensure that the element 50 does not interfere with the user's limb and is free to slide longitudinally within channel 52 without creating movement against child's skin. Typically, elongated surface element 50 is formed of plastic or any other suitable material, and can slide approximately 1 to 2 inches or longer in the proximal-distal direction within the channel 52, and therefore has the ability to accommodate any corrective forces initiated by the rest of orthotic device 10. Elongated surface element 50 must be long enough so that it does not exit channel 52 upon extreme motion of the user's foot.

FIGS. 3 to 7 show the first ankle joint 16a fixedly attached to the medial side of the distal receiving element 14, and the second ankle joint 16b is attached to elongated surface element 50 which is slidable within channel 52 on the lateral side of distal receiving element 14.

Figure 6:
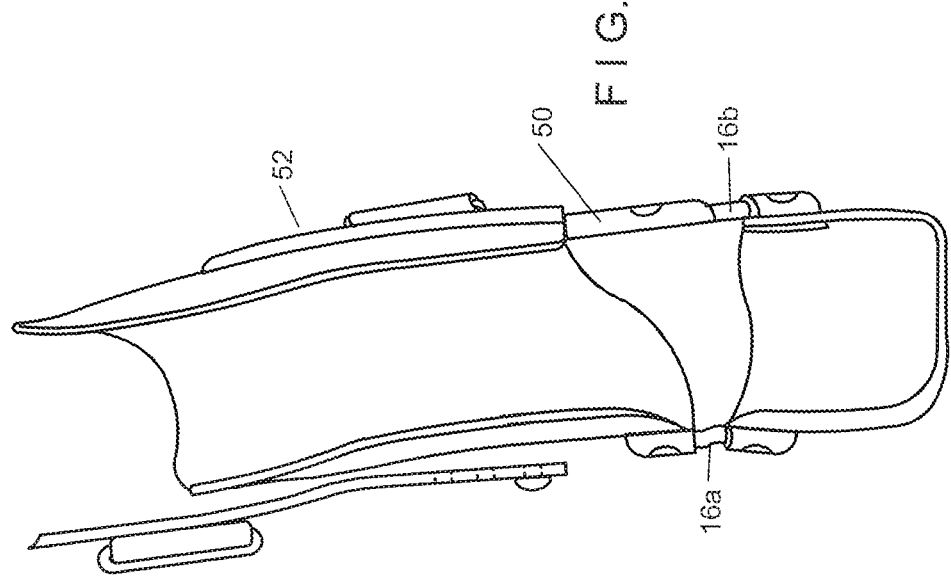
FIG. 6 is a lateral side elevational view of the distal portion of the orthotic device of FIG. 3, in a second, extended operative orientation.
Figure 7:
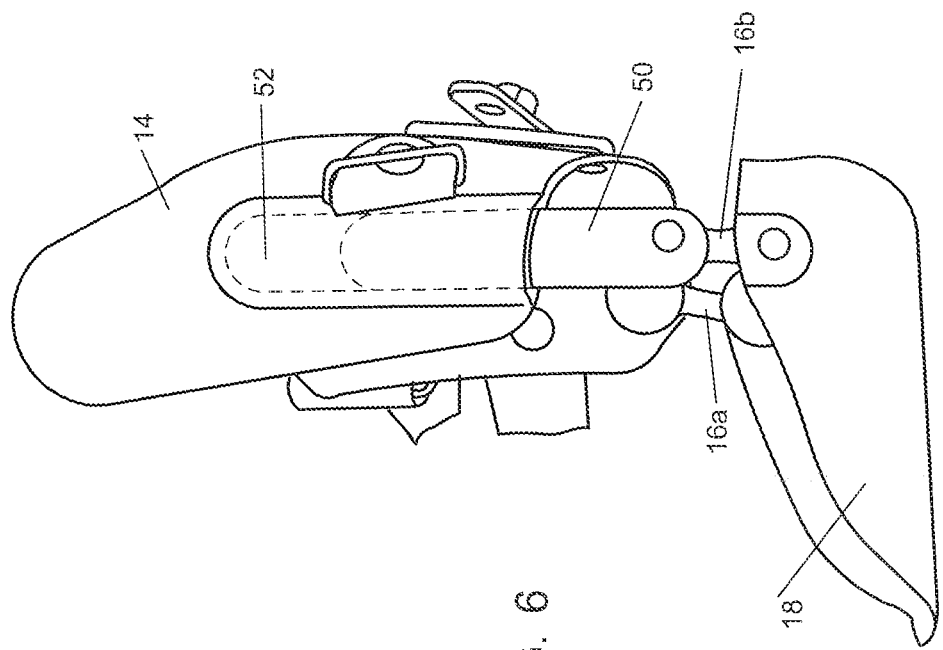
FIG. 7 is an anterior elevational view of the distal portion of the orthotic device of FIG. 6.

In FIGS. 3 and 5, the elongated surface element 50 is disposed mostly within channel 52, whereas in FIGS. 6 and 7 element 50 is shown to slide distally partly out of channel 52, thereby extending the length of the lateral side of the orthotic device 10, and accommodating an "air gap" between the foot receiving element 18 and the ground on the lateral side of the user's foot. This arrangement of the orthotic device 10 is particularly suitable when treating a Varus condition.

FIGS. 8 to 11 show the first ankle joint 16a fixedly attached to the lateral side of the distal receiving element 14 and to the corresponding portion of the foot receiving element 18. On the other hand, the second ankle joint 16b is fixedly attached to elongated surface element 50 which is slidable within channel 52 on the medial side of distal receiving element 14. The second ankle joint 16b is also attached to the foot receiving element 18.

In FIGS. 8 and 9, the elongated surface element 50 is disposed mostly within channel 52. However, in FIGS. 10 and 11 element 50 is shown to slide distally partly out of channel 52, thereby extending the length of the medial side of the orthotic device 10, and accommodating an "air gap" between the foot receiving element 18 and the ground on the lateral side of the user's foot. This arrangement of the orthotic device 10 is particularly suitable when treating a Valgus condition.

The orthotic device described in U.S. Pat. No. 7,147,612 discloses a single ankle joint on one side of the user's leg and is completely free on the opposing side. As such, there is a chance that the foot receiving element thereof would swing away from the distal receiving element on the side that does not include an ankle joint and expose the user's foot. In some situations, this might cause for the user to trip on and fall.

Orthotic device 10 of the present invention overcomes this problem by ensuring that the foot receiving element 18 is connected to the distal receiving element 14 on both sides, while one of the connections being dynamic to facilitate engagement of the user's foot with the floor at all times due to sliding motion of elongated element 50 within channel 52, Thus, the orthotic device of the present invention clearly provides a user with the advantages over the device of the prior art.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

What is claimed is:

1. An orthotic medical device, comprising:
   a proximal receiving element adapted to receive at least a portion of an upper area of a human limb, said proximal receiving element being substantially stationary with respect to said upper area of the limb a-re-a;
   a distal receiving element adapted to receive at least a portion of a lower area of said human limb, said distal receiving element having at least proximal and distal regions spaced from each other, said distal receiving element with said at least a portion of the lower area of the human limb being pivotally movable with respect to said proximal receiving element by forces applied at said proximal region of said distal receiving element;
   a foot supporting arrangement adapted to receive at least a portion of a foot of said human limb;
   a first ankle joint arrangement, fixedly attached to said foot supporting arrangement and to said distal region of said distal receiving element on a first side of said distal receiving element; and
   a second ankle joint arrangement, disposed on a second, opposing side, of said distal receiving element, including a rigid elongated element slidably disposed within a channel formed in said distal region of said distal receiving element, and an ankle joint fixedly attached to said foot supporting arrangement and to a distal end of said rigid elongated element,
   such that, on said second opposing side, distance of said foot supporting arrangement from said distal receiving element is dynamic and adjustable by sliding motion of said rigid elongated element within said channel in a distal/proximal direction.

2. The orthotic medical device according to claim 1, wherein said first side comprises a lateral side of said distal receiving element and said second opposing side comprises a medial side of said distal receiving element.

3. The orthotic medical device according to claim 1, wherein said first side comprises a medial side of said distal receiving element, and said second opposing side comprises a lateral side of said distal receiving element.

4. The orthotic medical device according to claim 1, wherein said first ankle joint arrangement is substantially rigid in the proximal to distal direction and is substantially flexible in the Coronal and Sagital planes.

5. The orthotic medical device according to claim 4, wherein the pivotal motion of the distal receiving element and the portion of the lower limb area received thereinside does not affect orientation of the bottom of the foot situated within the foot supporting arrangement with respect to the ground.

6. The orthotic medical device of claim 1, further comprising a proximal connecting element associated with said proximal receiving element, a distal connecting element associated with said distal receiving element, and a knee joint pivotally connecting said proximal and distal connecting elements.

7. The orthotic medical device according to claim 6, further comprising a resilient corrective element extending between the distal connecting element and the proximal region of the distal receiving element, and adapted to apply pivotal forces to said proximal region of said distal receiving element.

8. The orthotic medical device of claim 6, further comprising an adjustable member movable along said distal connecting element, and a medial connector extending outwardly from said adjustable member, so as to be associated with said distal receiving element and facilitate movement of said distal receiving element along said distal connecting element.

9. The orthotic medical device according to claim 8, wherein said adjustable member can be fixedly attached at a predetermined location on said distal connecting element and a pivotal connection is provided between said medial connector and said distal receiving element.

10. The orthotic medical device according to claim 8, wherein said proximal receiving element and said medial connector are fixedly positioned with respect to said knee joint.

11. The orthotic medical device according to claim 1, wherein said distal receiving element has a front longitudinal opening extending therethrough for insertion and receiving the lower leg limb area or a calf of the leg human limb of the user.

12. The orthotic medical device according to claim 11, wherein said channel extends substantially vertically within the body of the distal receiving element between an open end at the distal region and a closed end at the proximal region and is spaced from the front longitudinal opening.

* * * * *